US012207996B2

(12) United States Patent
Takaishi

(10) Patent No.: US 12,207,996 B2
(45) Date of Patent: Jan. 28, 2025

(54) UNDERPANTS-TYPE DISPOSABLE DIAPER

(71) Applicant: Daio Paper Corporation, Ehime (JP)

(72) Inventor: Mina Takaishi, Tochigi (JP)

(73) Assignee: Daio Paper Corporation, Ehime (JP)

( * ) Notice: Subject to any disclaimer, the term of this patent is extended or adjusted under 35 U.S.C. 154(b) by 756 days.

(21) Appl. No.: 17/051,520

(22) PCT Filed: May 24, 2019

(86) PCT No.: PCT/JP2019/020581
§ 371 (c)(1),
(2) Date: Oct. 29, 2020

(87) PCT Pub. No.: WO2019/235243
PCT Pub. Date: Dec. 12, 2019

(65) Prior Publication Data
US 2021/0236350 A1    Aug. 5, 2021

(30) Foreign Application Priority Data
Jun. 4, 2018   (JP) ................................. 2018-106828

(51) Int. Cl.
*A61F 13/494*   (2006.01)
*A61F 13/49*    (2006.01)
*A61F 13/496*   (2006.01)

(52) U.S. Cl.
CPC .. *A61F 13/49413* (2013.01); *A61F 13/49009* (2013.01); *A61F 13/49466* (2013.01); *A61F 13/496* (2013.01)

(58) Field of Classification Search
CPC .......... A61F 13/49413; A61F 13/49009; A61F 13/496; A61F 13/49446; A61F 13/495;
(Continued)

(56) References Cited

U.S. PATENT DOCUMENTS 5,509,915 A * 4/1996 Hanson .................. A61F 13/513
604/378
5,582,606 A * 12/1996 Bruemmer ............ A61F 13/511
604/385.28
(Continued)

FOREIGN PATENT DOCUMENTS

JP    H4-28363    1/1992
JP    H9-215709   8/1997
(Continued)

OTHER PUBLICATIONS

International Search Report for PCT/JP2019/020581, mailed Aug. 27, 2019.

*Primary Examiner* — Catharine L Anderson
*Assistant Examiner* — Quynh Dao Le
(74) *Attorney, Agent, or Firm* — Andrus Intellectual Property Law, LLP

(57) ABSTRACT

An underpants-type disposable diaper in which an inlet of a dorsal side barrier is easily opened wider. The above problem is solved by an underpants-type disposable diaper in which a barrier sheet extends to a back side of a position on a front side of a back end of an absorber from the position and extends outward in a width direction from positions of both side edges of the absorber in the width direction is included, the barrier sheet has a free part not bonded to a member on a back surface side and a fixed part bonded to the member on the back surface side, a pocket-shaped dorsal side barrier having an inlet opening to a crotch side is formed by the free part of the barrier sheet, and a torsion hardness of a predetermined part including a back end portion of the absorber is 0.18 to 0.32 N·cm/cm.

10 Claims, 14 Drawing Sheets

(58) Field of Classification Search
CPC ............ A61F 13/4942; A61F 13/494; A61F 13/49406; A61F 13/49019; A61F 13/49017; A61F 13/49061; A61F 13/49011–49014; A61F 2013/49493; A61F 13/49466

See application file for complete search history.

(56) References Cited

U.S. PATENT DOCUMENTS

| | | | | |
|---|---|---|---|---|
| 5,601,546 | A * | 2/1997 | Tanji | A61F 13/495 604/385.28 |
| 6,646,180 | B1 * | 11/2003 | Chmielewski | A61F 13/539 604/382 |
| 6,699,228 | B1 * | 3/2004 | Chmielewski | A61F 13/495 604/374 |
| 8,029,486 | B2 * | 10/2011 | Nakajima | A61F 13/4915 604/385.12 |
| 9,044,358 | B2 * | 6/2015 | Nakajima | A61F 13/49466 |
| 2006/0058767 | A1 * | 3/2006 | Zhang | A61F 13/495 604/385.24 |
| 2010/0326580 | A1 * | 12/2010 | Mori | A61F 13/49011 156/60 |
| 2012/0277703 | A1 * | 11/2012 | Rhein | A61F 13/49007 604/367 |
| 2014/0257228 | A1 * | 9/2014 | Wang | A61F 13/505 604/385.14 |
| 2016/0113823 | A1 * | 4/2016 | Iwasaki | A61F 13/4758 604/385.26 |
| 2016/0278996 | A1 * | 9/2016 | Takahashi | A61F 13/4942 |
| 2017/0246055 | A1 * | 8/2017 | Barnes | A61F 13/49011 |
| 2018/0104116 | A1 * | 4/2018 | Bishop | A61F 13/49466 |

FOREIGN PATENT DOCUMENTS

| | | | | |
|---|---|---|---|---|
| JP | H11-332913 | | 12/1999 | |
| JP | 2001-245922 | | 9/2001 | |
| JP | 2002-35029 | | 2/2002 | |
| JP | 2002-178428 | | 6/2002 | |
| JP | 2002-273808 | | 9/2002 | |
| JP | 2004-532758 | | 10/2004 | |
| JP | 2009-536845 | | 10/2009 | |
| JP | 2013074959 | A * | 4/2013 | |
| JP | 2015109900 | A * | 6/2015 | |
| JP | 2017-064226 | | 4/2017 | |
| JP | 2018-064698 | | 4/2018 | |
| WO | 2008/126708 | | 10/2008 | |
| WO | WO-2017056716 | A1 * | 4/2017 | ....... A61F 13/15203 |
| WO | 2017/138360 | | 8/2017 | |
| WO | 2017/141808 | | 8/2017 | |
| WO | WO-2018144058 | A1 * | 8/2018 | ............. A61F 13/49 |

* cited by examiner

[FIG.1]
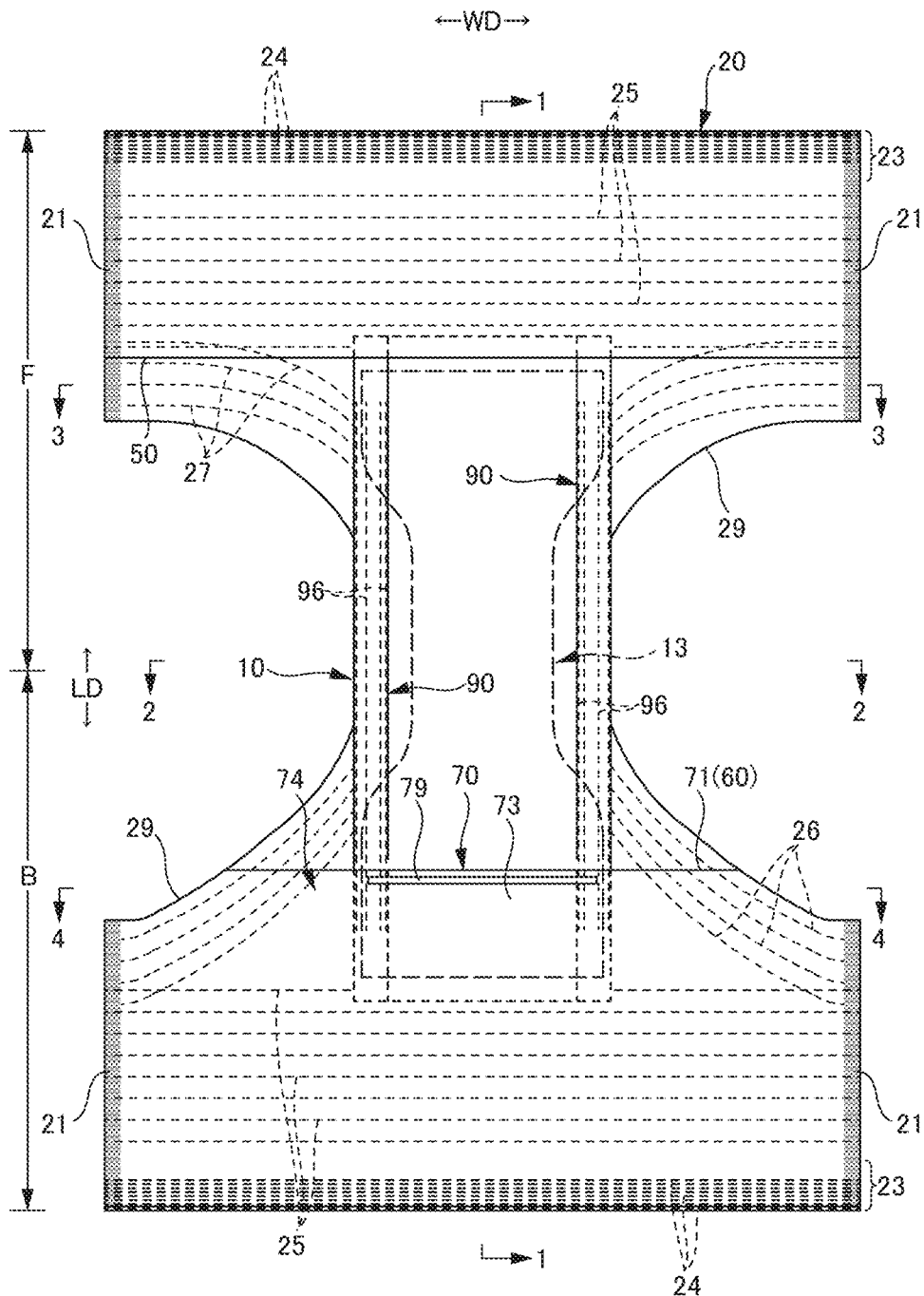

[FIG.2]
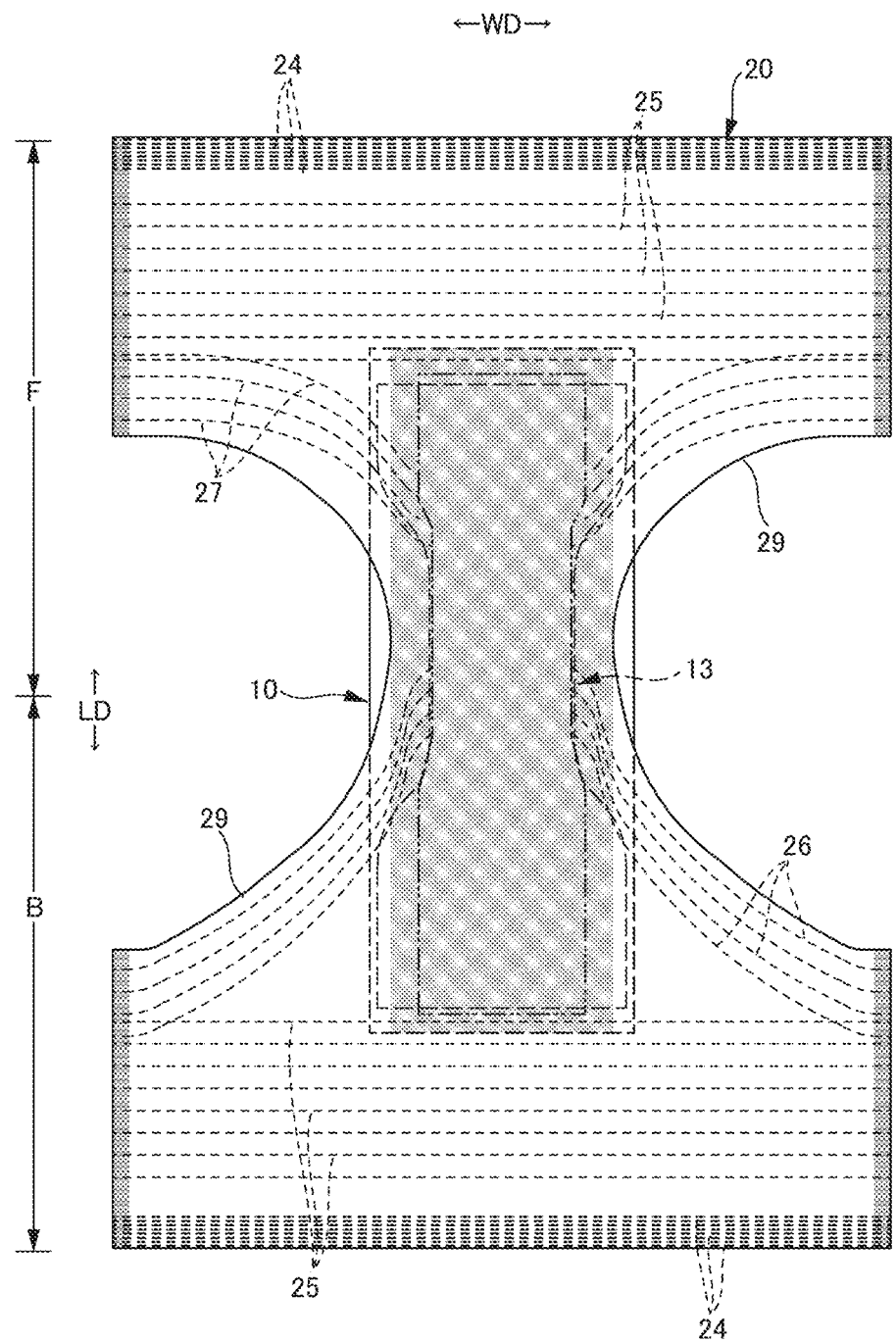

[FIG.3]
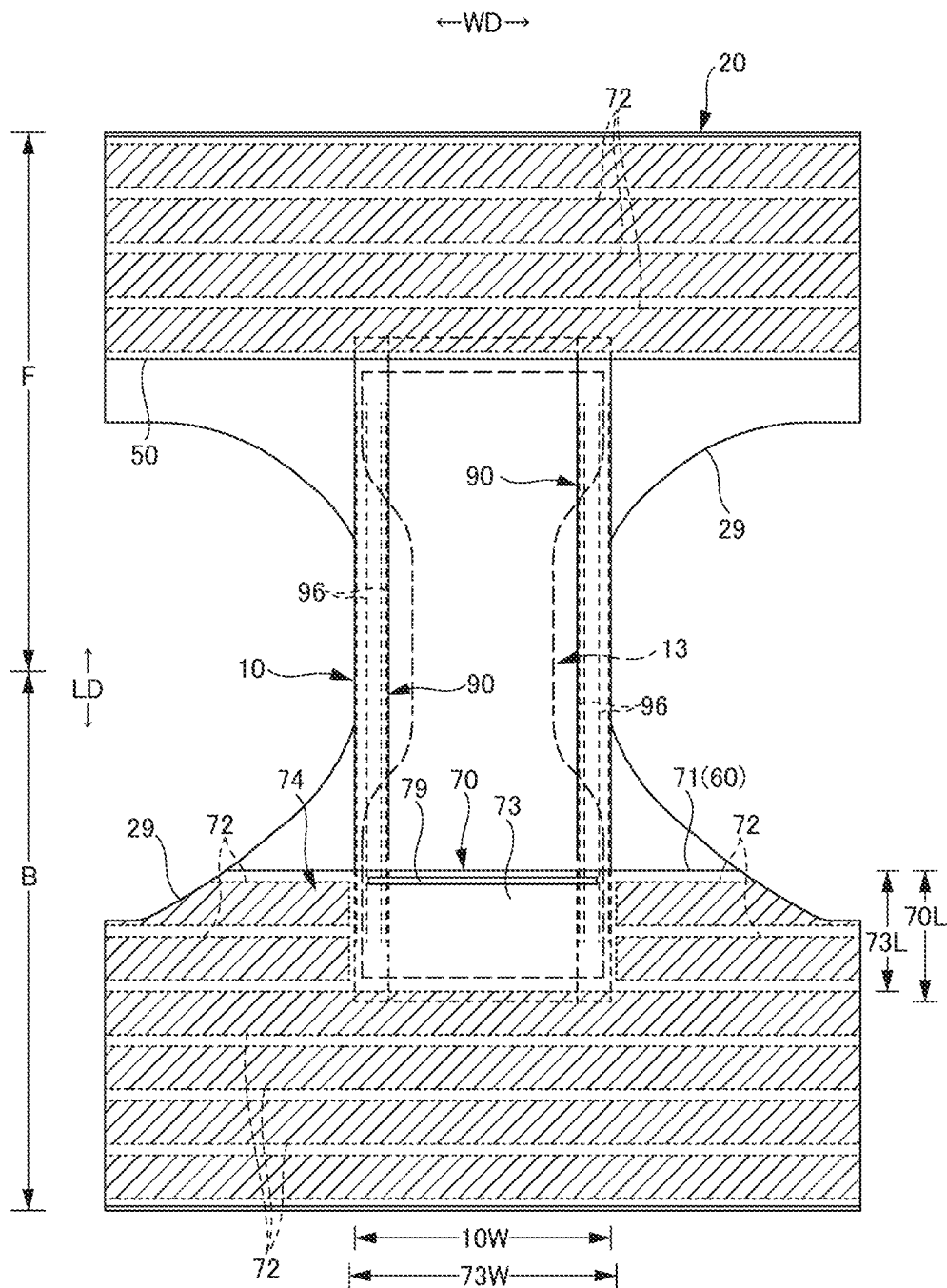

[FIG.4]
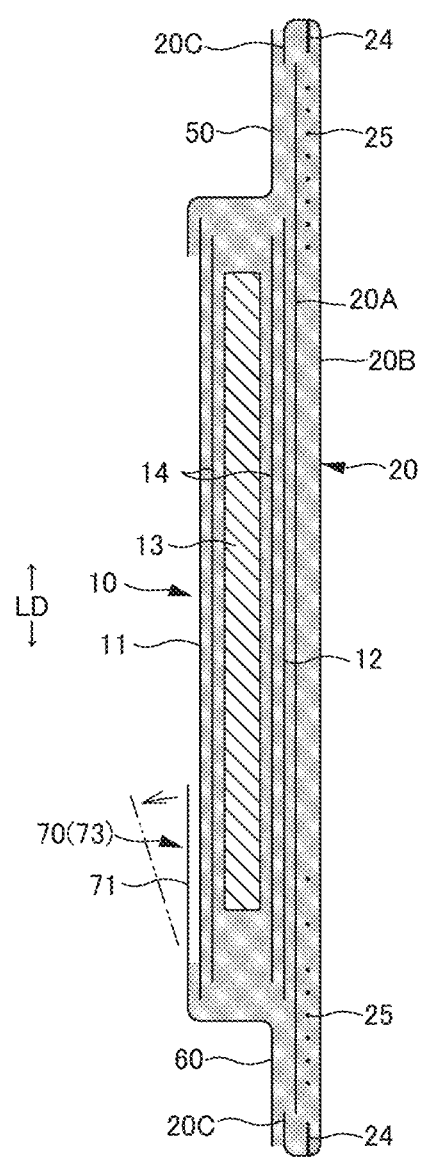

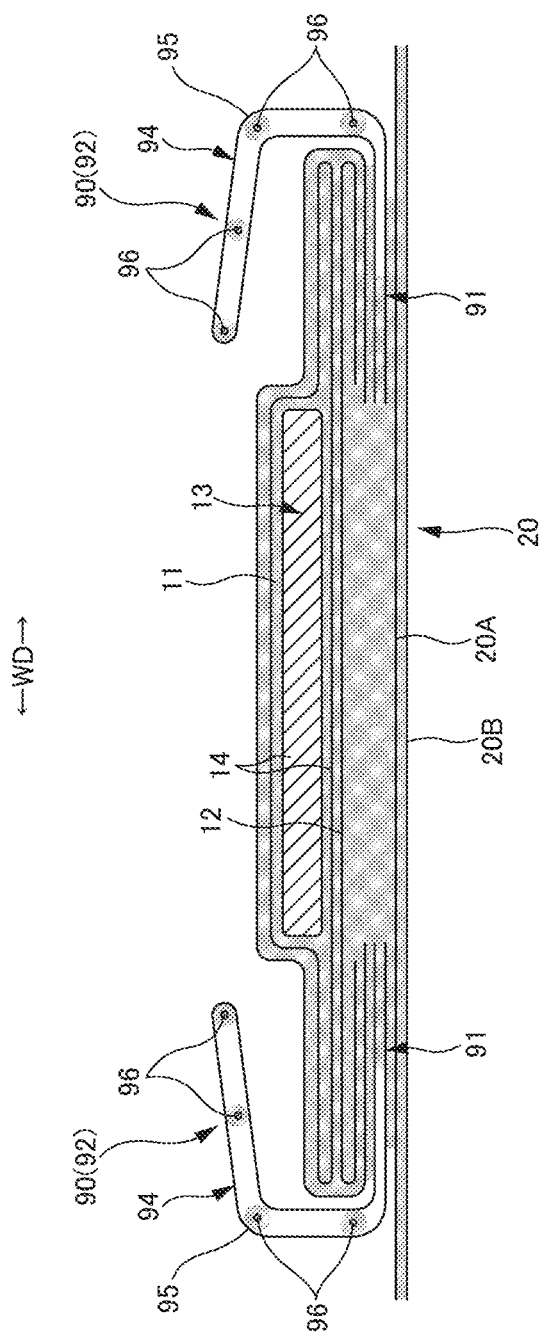

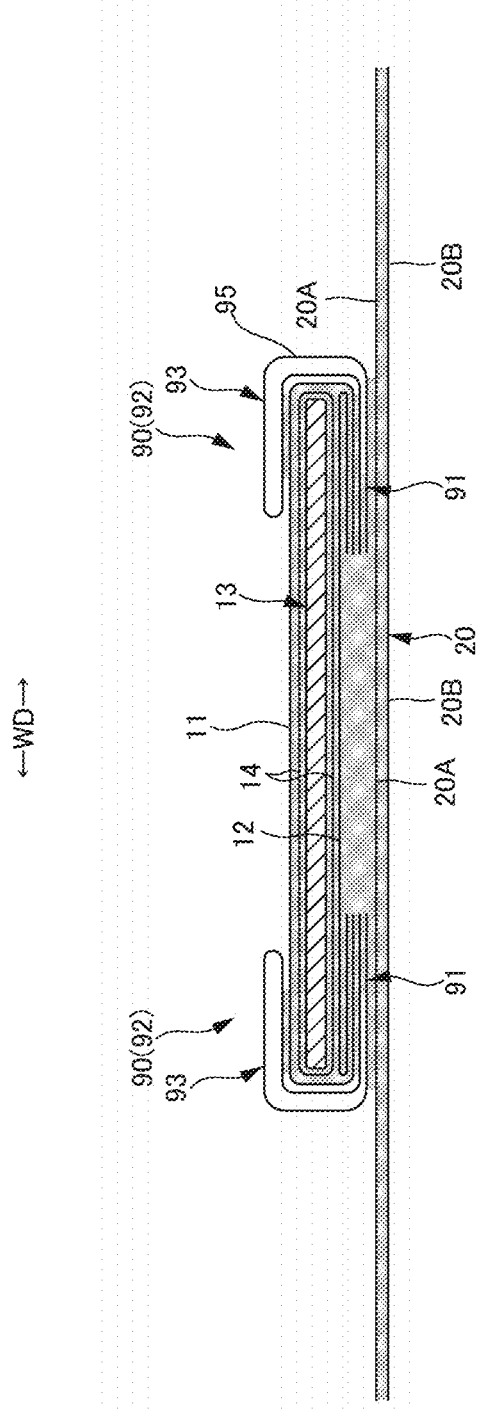

[FIG.7]
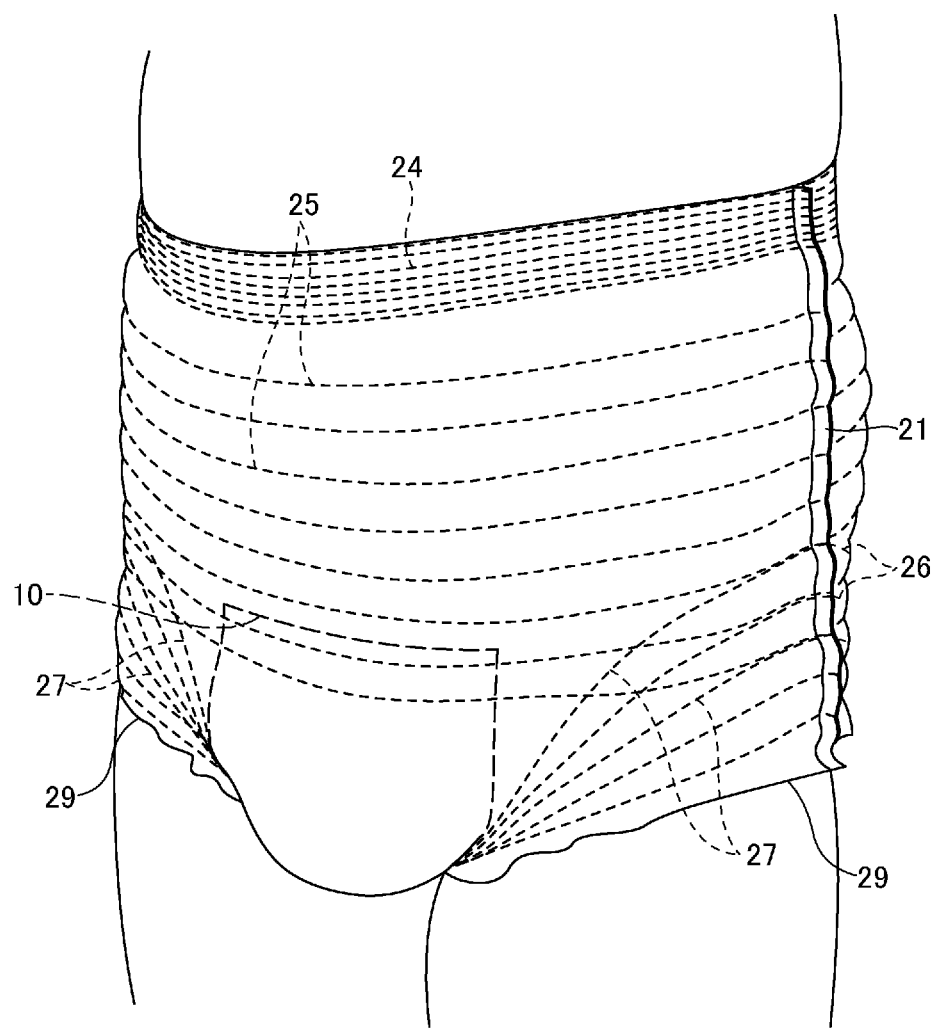

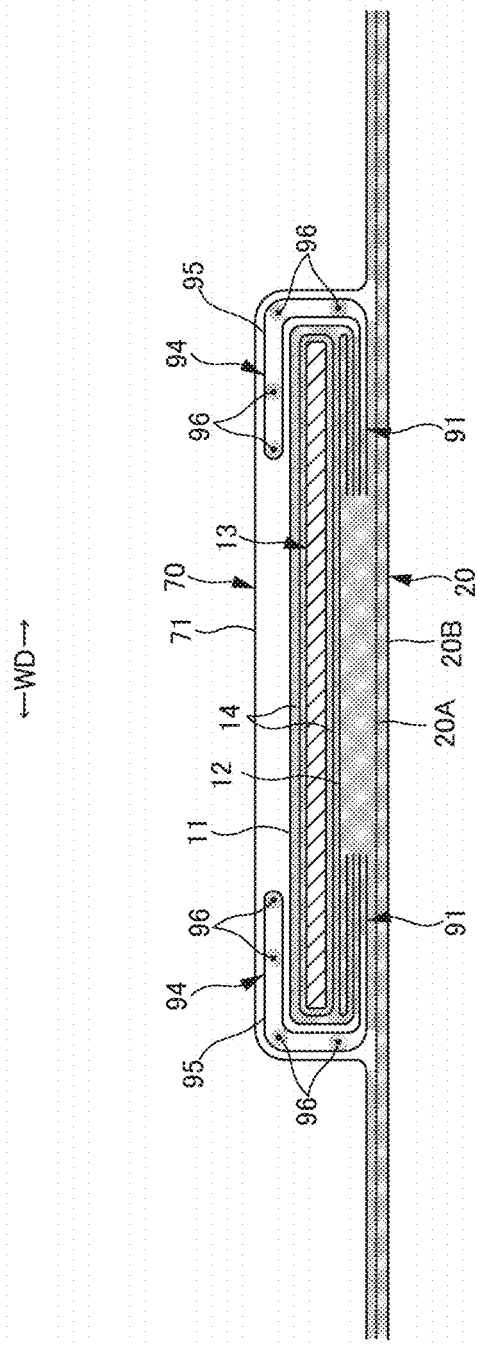
[FIG.8]

[FIG.9]
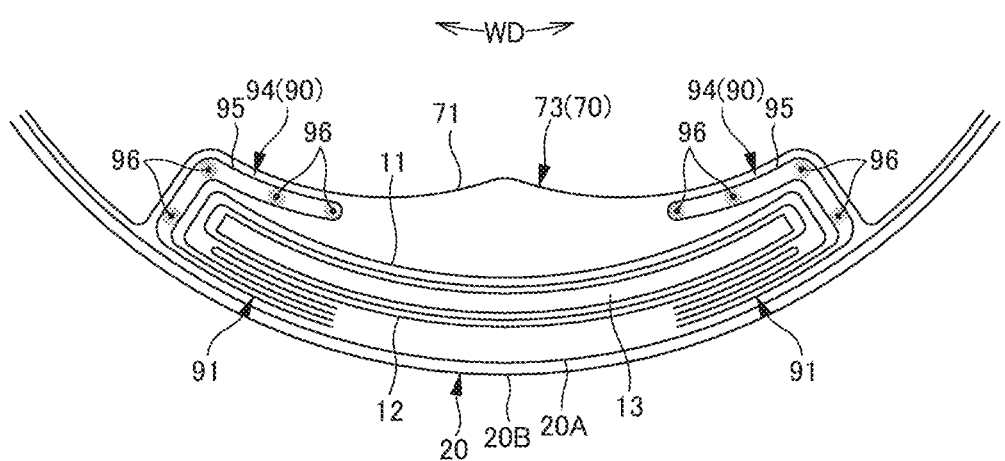

[FIG.10]
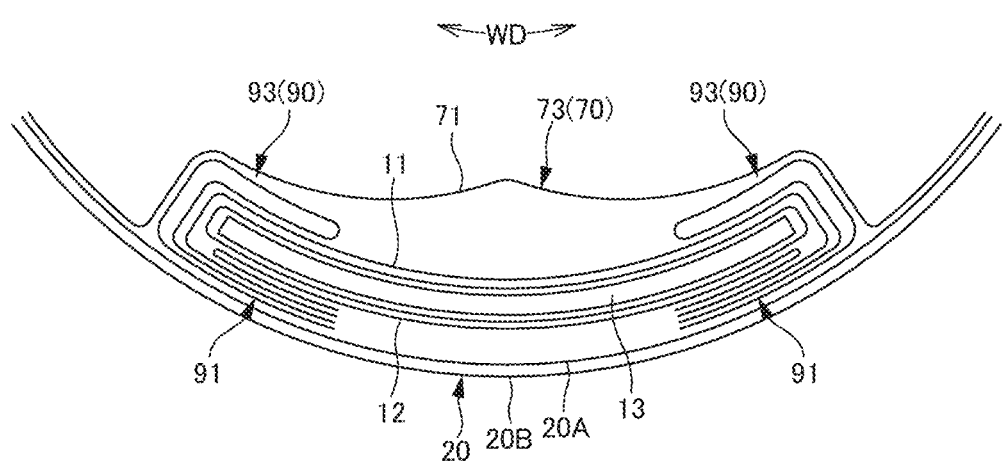

[FIG.11]
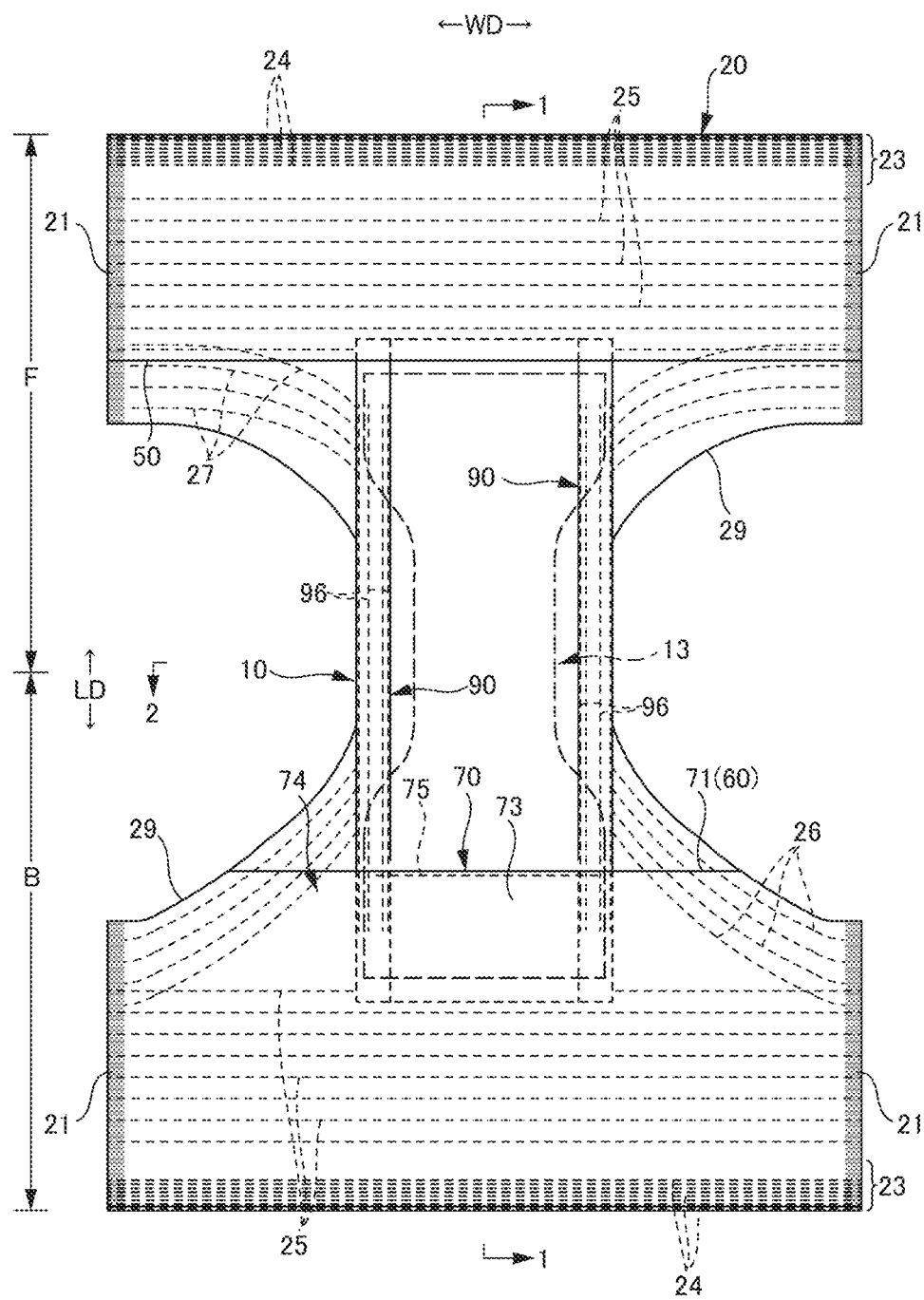

[FIG.12]
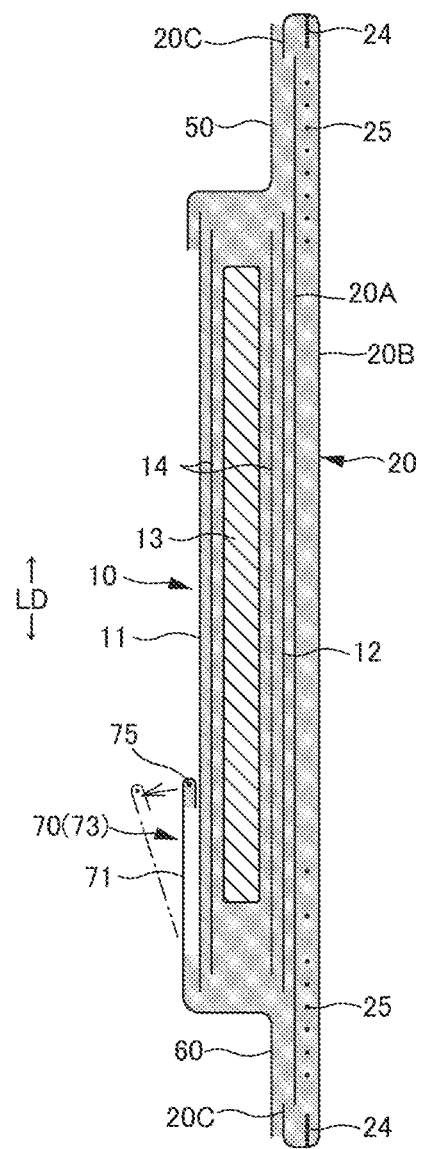

[FIG.13]
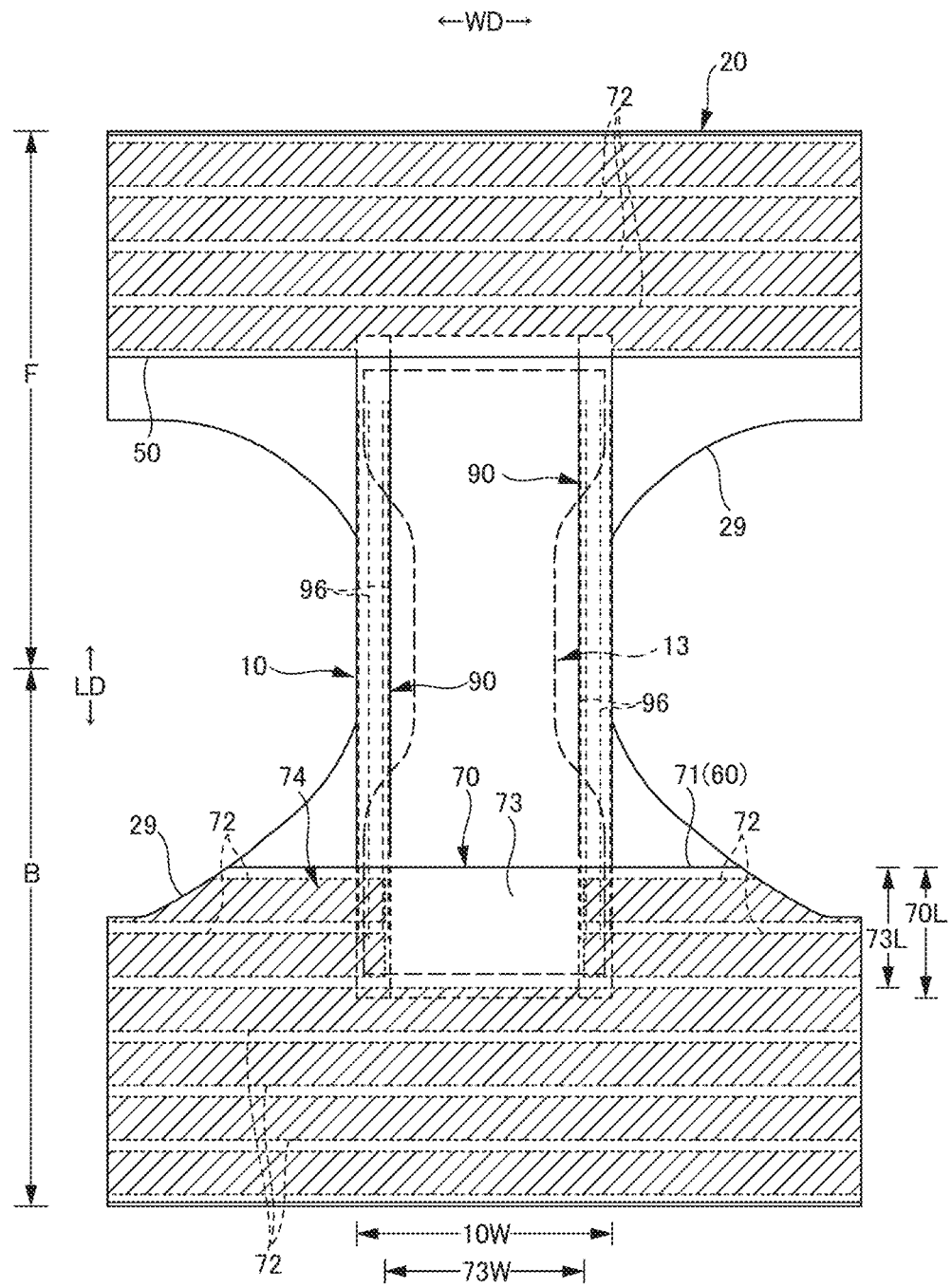

[FIG.14]
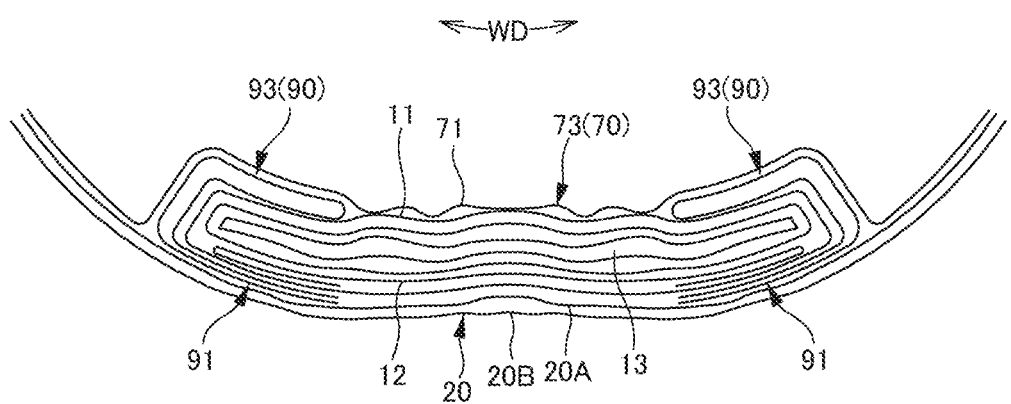

UNDERPANTS-TYPE DISPOSABLE DIAPER

CROSS-REFERENCE TO RELATED APPLICATIONS

This application is the U.S. national stage application of International Application PCT/JP2019/020581, filed May 24, 2019, which international application was published on Dec. 12, 2019, as International Publication WO 2019/235243 in the Japanese language. The International Application claims priority of Japanese Patent Application No. 2018-106828, filed Jun. 4, 2018. The international application and Japanese applications are both incorporated herein by reference, in entirety.

TECHNICAL FIELD

The present invention relates to an underpants-type disposable diaper having a back leakage prevention function.

BACKGROUND ART

In a tape-type disposable diaper in which both side portions of a dorsal side part are connected to an outer surface of a ventral side part, in general, a gap is likely to be generated between a back of a wearer and the diaper, and back leakage is likely to occur. Therefore, in the tape-type disposable diaper, it is preferred to use a pocket-shaped dorsal side barrier having an inlet on a crotch side on an inner surface of the dorsal side part (for example, see Patent Literatures 5 and 6).

On the other hand, the underpants-type disposable diaper has elasticity in a width direction in a lower torso region, and a gap is unlikely to be formed between a back of the wearer and the diaper. Thus, a situation in which excrement such as urine leaks from the back side (so-called back leakage) is unlikely to occur.

That is, a general underpants-type disposable diaper includes at least an outer body constituting a lower torso portion of a front body and a lower torso portion of a back body, and an inner body that includes an absorber and is attached to the outer body from the front body to the back body, in which both side edge portions of the outer body of the front body and both side edge portions of the outer body of the back body are bonded to form side seal portions, so that a waist opening and a pair of right and left leg openings are formed. Further, in the outer body, an elastic member is provided in a lower torso region determined as a front-back direction range having the side seal portions (front-back direction range from the waist opening to upper ends of the leg openings), so that elasticity in the width direction is added. As the elastic member, in addition to an elongated elastic member such as a rubber thread, an elastic film has been known. (For example, see Patent Literatures 1 to 4).

Due to such a high back leakage prevention property, there are users who actively use the underpants-type disposable diaper when sleeping for a long time such as at night. Needless to say, in such a use form, it is desirable to equip a dorsal side barrier even in the underpants-type disposable diaper.

However, the underpants-type disposable diaper has a problem that an inlet of the dorsal side barrier is likely to be narrowed due to the high fitting by the elastic member.

CITATION LIST

Patent Literature

Patent Literature 1: JP 2004-532758 A
Patent Literature 2: JP 2009-536845 A
Patent Literature 3: WO 2008/126708 A
Patent Literature 4: JP 2017-64226 A
Patent Literature 5: JP 2001-245922 A
Patent Literature 6: JP H9-215709 A

SUMMARY OF INVENTION

Technical Problem

Therefore, a main object of the invention is to provide an underpants-type disposable diaper in which the inlet of the dorsal side barrier is easily opened wider.

Solution to Problem

The underpants-type disposable diaper that solves the above problems is as follows.
<First Aspect>
An underpants-type disposable diaper including
 an integral outer body extending over a front body and a back body or an outer body separately provided to the front body and the back body,
 an inner body attached to an intermediate portion of the outer body in a width direction, the inner body extending over the front body and the back body,
 side seal portions obtained by bonding both side portions of the outer body in the front body and both side portions of the outer body in the back body, respectively,
 a waist opening and a pair of right and left leg openings,
 an absorber provided in a range including a back end portion of the inner body, and
 a stretchable region contracting in the width direction on a waist side of a back end portion of the absorber in the back body,
the underpants-type disposable diaper further including
 a barrier sheet that extends from a position on a front side of a back end of the absorber to a back side thereof and extends outward in the width direction from positions of both side edges of the absorber in the width direction,
 in which the barrier sheet has a free part not bonded to a member on a back surface side and a fixed part bonded to the member on the back surface side,
 the free part is located at least in a middle of a part overlapping the absorber in the width direction in the barrier sheet and is continuous from a front edge to a middle in a front-back direction in the barrier sheet,
 the fixed part surrounds a back side and both sides in the width direction of the free part, and a width direction inner edge of a part of the fixed part located on both sides of the free part in the width direction is on an outer side of a side edge of the inner body in the width direction and adjacent to the side edge of the inner body or is located on the inner body,
 a pocket-shaped dorsal side barrier having an inlet opening to a crotch side is formed by the free part of the barrier sheet, and
 a torsion hardness of a predetermined part including the back end portion of the absorber is 0.18 to 0.32 N·cm/cm.
(Function and Effect)
In this aspect, the pocket-shaped dorsal side barrier is formed by the barrier sheet that extends from a position on the front side of the back end of the absorber to the back side thereof and extends outward in the width direction from positions of the both side edges of the absorber in the width direction. Characteristically, the torsion hardness of the predetermined part including the back end portion of the absorber is 0.18 to 0.32 N·cm/cm, which is strong against deformation. As a result, a part of the absorber overlapping the free part of the barrier sheet gently bulges outward to circumscribe bulges of both gluteal regions, rippling deformation or bending deformation biting into an intergluteal cleft is less likely to occur, and contraction in the width direction becomes smaller. Further, the free part of the barrier sheet is raised on the opposite side from the bulge of the absorber based on the strong absorber that gently bulges outward to form the pocket-shaped dorsal side barrier having the inlet that opens on the crotch side. Therefore, the inlet of the dorsal side barrier is easily opened wider.

On the other hand, when the torsion hardness of the predetermined part including the back end portion of the absorber is excessively weak, a torsion force applied by movement of the legs and a contraction force in the width direction by the elastic member are applied to the part, so that rippling deformation or bending deformation biting into the intergluteal cleft occurs, and contraction in the width direction tends to increase. Further, in this case, the absorber serving as a base of the barrier sheet is less likely to bulge outward, and the width direction dimension of the free part of the barrier sheet becomes excessive, so that the free part of the barrier sheet becomes difficult to rise or is deformed in an irregular wavy pattern, and a situation in which the inlet or an inner space of the dorsal side barrier becomes unnecessarily narrow is likely to occur.

Note that a method for measuring the torsion hardness of the predetermined part including the back end portion of the absorber will be described later.

<Second Aspect>

The underpants-type disposable diaper according to the first aspect, in which the outer body does not have the stretchable region in an overlapping part between the free part of the barrier sheet and the absorber.

(Function and Effect)

As described above, when the part of the absorber overlapping the free part of the barrier sheet easily contracts in the width direction, the situation in which the inlet or the inner space of the dorsal side barrier becomes unnecessarily narrow is likely to occur. Therefore, as in this aspect, it is preferable that the overlapping part between the free part of the barrier sheet and the absorber does not have the stretchable region.

<Third Aspect>

The underpants-type disposable diaper according to the first or second aspect, in which in the predetermined part including the back end portion of the absorber, a total basis weight of pulp fibers and super absorbent polymer particles is 350 to 600 g/m², a weight ratio of the super absorbent polymer particles to the pulp fibers is 40 to 60%, and a thickness is 6 to 12 mm.

(Function and Effect)

In the technical field of the underpants-type disposable diaper, an aggregate of pulp fibers and super absorbent polymer particles is widely used as the absorber. In the case of using such an absorber, by making the pulp basis weight sufficiently high and having a sufficient thickness as in this aspect, it is possible to obtain the absorber having the above-mentioned torsion hardness.

<Fourth Aspect>

The underpants-type disposable diaper according to any one of the first to third aspects, in which the free part of the barrier sheet does not have a stretchable part in the width direction contracted by an elastic member.

(Function and Effect)

In a conventional dorsal side barrier, an elastic member is attached to a front end portion of a free part of a barrier sheet to raise the free part by a contraction force of the elastic member in many cases. On the other hand, as described above, in a case where the free part of the barrier sheet rises on the opposite side from the bulge of the absorber based on the strong absorber that gently bulges outward, even when the elastic member is not provided, the free part of the barrier sheet is slightly pushed toward the center side in the width direction, and thus naturally easily rises to the opposite side from the bulge of the absorber. Therefore, as in this aspect, it is also preferable to simplify the structure and thereby reduce the cost without providing a stretchable part in the width direction contracted by the elastic member in the free part of the barrier sheet.

<Fifth Aspect>

The underpants-type disposable diaper according to the fourth aspect, in which a mark is provided to a front end portion in the free part of the barrier sheet.

(Function and Effect)

In particular, in the case of not having the elastic member for raising the free part of the barrier sheet, when the barrier sheet appears to merge into the surrounding member, for example, in a case where the free part of the barrier sheet is improperly bent, a user may not notice this fact during use, and there is concern that the leakage prevention effect may be insufficient. Therefore, as in this aspect, it is also preferable to provide a mark at the front end portion in the free part of the barrier sheet so that the presence of the barrier sheet can be easily noticed.

<Sixth Aspect>

The underpants-type disposable diaper according to the fourth or fifth aspect, in which the inner body has rising gathers that rise from both sides in the width direction, each of the rising gathers has a main unit part extending from both side portions of a surface of the inner body to a center side in the width direction, a fallen portion which is a part fixed to the surface of the inner body in a fallen state of both end portions of the main unit part in the front-back direction, a non-fixed rising part located between front and back fallen portions, and a gather elastic member provided along the front-back direction at least at a tip portion of the rising part, the barrier sheet is provided to pass over the rising gathers, and at least a part of the barrier sheet overlaps the rising parts of the rising gathers.

(Function and Effect)

In particular, in the case of not having the elastic member for raising the free part of the barrier sheet, there is concern that rising of the free part of the barrier sheet may be insufficient. Therefore, as in this aspect, it is preferable that the free part of the barrier sheet is raised by the rising parts of the rising gathers normally provided on both sides of the inner body in the width direction.

<Seventh Aspect>

The underpants-type disposable diaper according to any one of the fourth to sixth aspects, in which at least an outer surface of the barrier sheet is a nonwoven fabric of fibers which is made of polyethylene resin.

(Function and Effect)

A nonwoven fabric of polyethylene fiber has a property of easily adhering to the skin. Therefore, it is preferable to use the nonwoven fabric of this aspect as the above-mentioned barrier sheet.

Advantageous Effects of Invention

As described above, the invention is advantageous in that the inlet of the dorsal side barrier is easily opened wider.

BRIEF DESCRIPTION OF DRAWINGS

FIG. 1 is a plan view (internal surface side) of an underpants-type disposable diaper in a spread state.

FIG. 2 is a plan view (external surface side) of the underpants-type disposable diaper in the spread state.

FIG. 3 is a plan view (internal surface side) illustrating a main part of the underpants-type disposable diaper in the spread state.

FIG. 4 is a cross-sectional view taken along line 1-1 in FIG. 1.

FIG. 5 is a cross-sectional view taken along line 2-2 in FIG. 1.

FIG. 6 is a cross-sectional view taken along line 3-3 in FIG. 1.

FIG. 7 is a perspective view of the underpants-type disposable diaper in a worn state.

FIG. 8 is a cross-sectional view taken along line 4-4 in FIG. 1.

FIG. 9 is a cross-sectional view illustrating a main part in the worn state.

FIG. 10 is a cross-sectional view illustrating the main part in the worn state.

FIG. 11 is a plan view (internal surface side) of the underpants-type disposable diaper in the spread state.

FIG. 12 is a cross-sectional view taken along line 1-1 in FIG. 11.

FIG. 13 is a plan view (internal surface side) illustrating the main part of the underpants-type disposable diaper in the spread state.

FIG. 14 is a cross-sectional view illustrating the main part in the worn state.

DESCRIPTION OF EMBODIMENTS

Hereinafter, an example of an underpants-type disposable diaper will be described in detail with reference to the accompanying drawings. Note that a dotted pattern portion in the figures indicates an adhesive as bonding means that bonds respective components located on the front surface side and the back surface side thereof, and is formed by solid, bead, curtain, summit, spiral coating of a hot melt adhesive, pattern coating (transfer of the hot melt adhesive in a letterpress method), etc., or application of an elastic member to an outer peripheral surface such as comb gun or sure wrap application instead of or together with the above methods in a fixed part of the elastic member. Examples of the hot melt adhesive include EVA-based, pressure sensitive adhesion rubber-based (elastomer-based), polyolefin-based, and polyester/polyamide-based adhesives, and can be used without any particular limitation. As bonding means that bonds respective components, it is possible to use means by material welding such as heat sealing or ultrasonic sealing.

FIGS. 1 to 7 illustrate the underpants-type disposable diaper. This underpants-type disposable diaper (hereinafter also simply referred to as a diaper) has an integral outer body 20 extending over a front body F and a back body B, and an inner body 10 fixed to an inner surface of the outer body 20 to extend from the front body F to the back body B, and the inner body 10 is obtained by interposing an absorber 13 between a liquid pervious top sheet 11 and a liquid impervious sheet 12. In manufacturing, after a back surface of the inner body 10 is bonded to an inner surface (upper surface) of the outer body 20 by bonding means such as a hot melt adhesive (dotted pattern portion in FIG. 2), the inner body 10 and the outer body 20 are folded at a center in a front-back direction LD (vertical direction), which is a boundary between the front body F and the back body B, and both side portions thereof are bonded by heat welding, a hot melt adhesive, etc. to form side seal portions 21, thereby forming the underpants-type disposable diaper in which a waist opening and a pair of right and left leg openings are formed. The outer body 20 may be separately provided on the front body F and the back body B.

(Example of Structure of Inner Body)

As illustrated in FIGS. 4 to 6, the inner body 10 has a structure in which the absorber 13 is interposed between the top sheet 11 and the liquid impervious sheet 12, and absorbs and retains the excreted liquid passing through the top sheet 11 by the absorber 13. A planar shape of the inner body 10 is not particularly limited, and is generally a substantially rectangular shape as in the illustrated embodiment.

As the top sheet 11 that covers the front surface side (skin contact surface side) of the absorber 13, a perforated or non-perforated nonwoven fabric, a porous plastic sheet, etc. is preferably used. As a raw material fiber included in the nonwoven fiber, in addition to synthetic fibers such as polyolefin-based fiber such as polyethylene or polypropylene, polyester-based fiber, and polyamide-based fiber, it is possible to use regenerated fibers such as rayon and cupra, and natural fibers such as cotton, and it is possible to use a nonwoven fabric obtained by an appropriate processing method such as a spun lace method, a spun bond method, a thermal bond method, an air through method, or a needle punch method. Among these processing methods, the spun lace method is excellent in flexibility and drapability, and the thermal bond method is excellent in bulkiness and softness. When a plurality of through holes are formed in the top sheet 11, urine, etc. can be rapidly absorbed. In the illustrated embodiment, the top sheet 11 extends up to the back surface side of the absorber 13 with the side edge portions of the absorber 13 wrapped around.

As the liquid impervious sheet 12 covering the back surface side of the absorber 13 (non-skin contact surface side), a liquid impervious plastic sheet of polyethylene, polypropylene, etc. is used. However, in recent years, a sheet having moisture permeability is preferably used from a viewpoint of preventing stuffiness. As this water blocking and moisture-permeable sheet, for example, it is possible to preferably use a microporous sheet obtained by melt kneading inorganic fine particles such as calcium carbonate in a polyolefin resin such as polyethylene or polypropylene to form a sheet, and then monoaxially or biaxially stretching the sheet. In the illustrated embodiment, the liquid impervious sheet 12 is folded back to the back surface side on both sides of the absorber 13 in the width direction WD together with the top sheet 11. However, the invention is not limited to such a structure, and another known structure can be adopted.

As the absorber 13, it is possible to use a known one, for example, an accumulates of pulp fibers, an assembly of filaments such as cellulose acetate, or one having a nonwoven fabric as a base and a super absorbent polymer mixed and fixed therein as necessary. An overall shape of the absorber 13 can be an appropriate shape such as a rectangular shape as well as a substantially hourglass shape having a narrowing part narrower than both front and back sides in the crotch part. The absorber 13 can be provided only in a partial range of the inner body 10 as long as the absorber 13 is provided in a range including a back end portion of the inner body 10. In a normal case, it is desirable that the absorber 13 is provided over almost the entire region excluding the front and back end portions of the inner body 10.

The absorber 13 can be wrapped with a wrapping sheet 14 such as crepe paper having the liquid pervious property and liquid holding property to hold the shape and the polymer as necessary. As the wrapping sheet 14, tissue paper, particularly crepe paper, a nonwoven fabric, a polyethylene laminated nonwoven fabric, a sheet with small holes, etc. can be used. However, it is desirable that the wrapping sheet be a sheet through which the super absorbent polymer particles do not pass. When a nonwoven fabric is used instead of the crepe paper, a hydrophilic SMS nonwoven fabric (SMS, SSMMS, etc.) is particularly suitable, and polypropylene, polyethylene/polypropylene composite material, etc. can be used as a material. The basis weight of the wrapping sheet 14 is desirably 5 to 40 $g/m^2$, particularly desirably 10 to 30 $g/m^2$.

A wrapping mode of the wrapping sheet 14 can be appropriately determined. However, from a viewpoint of ease of manufacturing and prevention of leakage of super absorbent polymer particles from edges of front and back end portions, a preferable mode is that the absorber 13 is wound in a tubular shape to surround front and back surfaces and both side surfaces, front and back edge portions are projected from the front and back of the absorber 13, and wound and overlapped parts and overlapping parts of front and back protrusions are bonded by bonding means such as a hot melt adhesive or material welding.

Rising gathers 90 are provided on both sides of the inner body 10 in the width direction WD. The rising gathers 90 have rising parts 94 rising from side portions of the inner body 10, and the rising parts 94 are in contact with a range from a groin portion of the wearer to a gluteal region through a leg circumference to prevent side leakage. More specifically, as illustrated in FIGS. 5 and 6, each of the rising gathers 90 of the illustrated example has a gather fixed portion 91 fixed to a side portion of a back surface of the inner body 10, a main unit part 92 extending from the gather fixed portion 91 to a side portion of a front surface of the inner body 10 through a side of the inner body 10, a fallen portion 93 formed by fixing front and back end portions of the main unit part 92 to the side portion of the front surface of the inner body 10 in a fallen state, and a rising part 94 formed by not fixing between fallen portions 93. Further, these parts have a two-layered structure formed by folding back the gather sheet 95, and between the layers, an elongated gather elastic member 96 is arranged at a tip portion of the rising part 94, etc. With such a structure, the rising part 94 of the rising gather 90 rises to come into contact with a skin of the wearer. As the gather sheet 95, a water repellent nonwoven fabric is preferably used.

Examples of the gather elastic member 96 include a commonly used material such as polystyrene-based rubber, polyolefin-based rubber, polyurethane-based rubber, polyester-based rubber, polyurethane, polyethylene, polystyrene, styrene-butadiene copolymer, silicone, or polyester. Further, in order to make it difficult to see from the outside, it is preferable that the thickness is 925 dtex or less, the tension is 150 to 350%, and the interval is 7.0 mm or less. Note that as the gather elastic member 96, in addition to a thread-shaped member as in the illustrated embodiment, it is possible to use a tape-shaped member having a certain width.

As a row material fiber included in the gather sheet 95, similarly to the top sheet 11, in addition to synthetic fibers such as polyolefin-based fiber such as polyethylene or polypropylene, polyester-based fiber, and polyamide-based fiber, it is possible to use regenerated fibers such as rayon and cupra, and natural fibers such as cotton, and it is possible to use a nonwoven fabric obtained by an appropriate processing method such as a spun bond method, a thermal bond method, an air through method, or a needle punch method. In particular, in order to prevent stuffiness, it is preferable to use a nonwoven fabric having a low basis weight and excellent air permeability. Further, with regard to the gather sheet 95, in order to prevent the permeation of urine, etc., prevent the rash, and enhance the texture (dry feeling), it is desirable to use a water-repellent nonwoven fabric coated with a silicone-based, paraffin metal-based, alkylchromic chloride-based water repellent agent, etc.

(Example of Structure of Outer Body)

As illustrated in FIGS. 4 to 6, the outer body 20 has a two-layered structure including a pressing sheet 20A and a back sheet 20B, each of which is made of a nonwoven fabric, etc., elastic members 24 to 27 are provided between the pressing sheet 20A and the back sheet 20B, and between nonwoven fabrics of a folded part 20C formed by folding back the back sheet 20B toward the internal surface side at the waist opening edge, and the outer body 20 contracts by the contraction force of the elastic members 24 to 27 in a natural length state, so that the outer body 20 is given elasticity. A planar shape of the outer body 20 is substantially an hourglass shape as a whole by concave around-leg lines 29 formed to form leg openings at both sides in the middle in the front-back direction LD.

The outer body 20 of the illustrated embodiment includes, as the elastic member, in a spread shape illustrated in FIGS. 1 and 2, a waist portion elastic member 24 arranged near a waist opening 23 and a plurality of lower waist portion elastic members 25 arranged along the width direction WD at an interval in the vertical direction in the front body F and the back body B. Further, in each of the front body F and the back body B, separately from the lower waist portion elastic members 25, the outer body includes a plurality of curved elastic members 26 and 27 which are directed from one side seal portion 21 to the crotch part along one leg opening, traverse the crotch part, and extend while curving in a pattern reaching the other side seal portion 21 along the other leg opening, and are arranged at an interval without intersecting each other. These elastic members 24 to 27 are fixed in a state of being extended at a predetermined stretch rate along an extending direction thereof. Note that in the outer body 20, so-called around-leg elastic members that are continuous from the side seal portions of the front body F to the side seal portions of the back body B along the around-leg lines 29 are not provided.

The waist portion elastic member 24 is an elongated elastic member such as a plurality of rubber threads arranged at an interval in the vertical direction near a waist opening edge within a range of the side seal portions 21 where the front body F and the back body B are bonded, and is used to wear the diaper on the body by giving a stretching force to tighten the waist of the body. As the waist portion elastic member 24, the rubber threads are used in the illustrated example. However, for example, it is possible to use a tape-shaped stretchable member. In addition, even though the waist portion elastic member 24 of the illustrated embodiment is interposed between the nonwoven fabrics of the folded part 20C of the back sheet 20B in the waist portion, the waist portion elastic member 24 may be interposed between the pressing sheet 20A and the back sheet 20B.

The lower waist portion elastic member 25 is an elongated elastic member such as rubber threads arranged at an interval in the vertical direction over a range roughly from an upper portion to a lower portion in the side seal portions 21, and is used to apply a stretching force in the width direction WD to each of around-waist parts of the front body F and the back body B, so that the diaper is brought into close contact with the body. Note that a boundary between the waist portion elastic member 24 and the lower waist portion elastic member 25 may not be clear. For example, among the elastic members arranged in the width direction WD in the front body F and the back body B at intervals in the vertical direction, even though the number may not be specified, it is sufficient that some of the elastic members on the upper portion side function as the waist portion elastic member, and the remaining elastic members function as the lower waist portion elastic member.

In the back body B, the dorsal side curved elastic member 26, which is arranged separately from the lower waist portion elastic member 25, is an elongated elastic member such as rubber thread, and is arranged along a predetermined curve. The dorsal side curved elastic member 26 may be one member and is preferably a plurality of members. In the illustrated example, the dorsal side curved elastic member 26 is an elongated elastic member of four rubber threads, etc., and these dorsal side curved elastic members 26 are arranged at intervals without intersecting each other. The dorsal side curved elastic member 26 is not arranged substantially in a bundle with a few elastic members closely spaced, and three or more, preferably four or more dorsal side curved elastic members 26 are arranged at intervals of about 3 to 20 mm, preferably 6 to 16 mm to form a predetermined stretchable zone.

In the front body F of the outer body 20, the ventral side curved elastic member 27, which is arranged separately from the lower waist portion elastic member 25, is an elongated elastic member such as rubber thread, and is arranged along a predetermined curve. The ventral side curved elastic member 27 may be one member and is preferably a plurality of members. In the illustrated example, the ventral side curved elastic member 27 is four thread-shaped elastic members, and these ventral side curved elastic members 27 are arranged at intervals without intersecting each other. The ventral side curved elastic member 27 is not arranged substantially in a bundle with a few elastic members closely spaced, and three or more, preferably four or more dorsal side curved elastic members 26 are arranged at intervals of about 3 to 20 mm, preferably 6 to 16 mm to form a predetermined stretchable zone.

Note that as illustrated in FIG. 2, after continuously fixing the lower waist portion elastic member 25 and the curved elastic members 26 and 27 arranged in the front body F and the back body B to the outer body 20 during manufacturing, an intermediate portion (part surrounded by a two-dot chain line in the figure) of a part overlapping the absorber 13 in the width direction WD can be finely cut in a predetermined cutting pattern to form a non-contraction part on which a contraction force does not act, and a part laterally extending from the non-contraction part can be set to a contraction part on which the contraction force acts (that is, a part in which the lower waist portion elastic member 25 and the curved elastic members 26 and 27 are continuously left). In this way, it is possible to prevent unnecessary contraction of the inner body (in particular, the absorber 13) in the width direction WD. Naturally, the lower waist portion elastic member 25 and the curved elastic members 26 and 27 can be continuously arranged across the inner body 10.

As can be seen from this example, the contraction part in a site where the elastic members 24 to 27 are arranged becomes the stretchable region. The stretchable region may be provided only on the waist side of the back end portion of the absorber 13 in the back body B, and may be provided in each portion as in the illustrated example or another known example.

For example, the above-mentioned outer body 20 can be manufactured by technologies described in JP H4-28363 A and JP H11-332913 A. In addition, to cut the curved elastic members 26 and 27 on the inner body 10 and make the curved elastic members 26 and 27 discontinuous, cutting methods described in JP 2002-35029 A, JP 2002-178428 A, and JP 2002-273808 A are preferably adopted.

Unlike the illustrated example, the curved elastic members 26 and 27 may be provided only on one of the front body F and the back body B. In addition, when the curved elastic members 26 and 27 are provided on both the front body F and the back body B, it is possible to adopt a mode (not illustrated) in which a part or all of a group of the curved elastic members 27 arranged on the front body F side intersects with a part or all of a group of the curved elastic members 26 arranged on the back body B. However, as in the illustrated example, it is preferable to adopt a mode in which the group of the curved elastic members 27 arranged on the front body F side does not intersect with the group of the curved elastic members 26 arranged on the back body B, and the groups are spaced apart in the vertical direction in the intermediate portion in the front-back direction LD, particularly at a position slightly biased to the front body F.

Further, the curved elastic members 26 and 27 may not be entirely curved, and may have a partially linear part.

Stretch rates of the elastic members 24 to 27 during fixing can be appropriately determined. However, in the case of using for normal adults, the stretch rate of the waist portion elastic member 24 can be set to about 160 to 320%, the stretch rate of the lower waist portion elastic member 25 can be set to about 160 to 320%, and the stretch rates of the curved elastic members 26 and 27 can be set to about 230 to 320%.

(Cover Sheet)

As illustrated in FIGS. 1 and 4, to cover the front and back end portions of the inner body 10 attached on the inner surface of the outer body 20 and prevent leakage from front and back edges of the inner body 10, cover sheets 50 and 60 may be provided. The illustrated embodiment will be more specifically described. The cover sheet 50 on the front side extends over the entire part in the width direction WD from the inner surface of the folded part 20C at a waist side end portion in the inner surface of the front body F to a position overlapping the front end portion of the inner body 10, and the cover sheet 60 on the back side extends over the entire part in the width direction WD from the inner surface of the folded part 20C at a waist side end portion in the inner surface of the back body B to a position overlapping the back end portion of the inner body 10. When a slight non-adhesive part is provided over the entire part in the width direction WD (may be only a center portion) at a crotch side edge portion of each of the cover sheets 50 and 60, the adhesive does not stick out, and this part can be made slightly rise from the top sheet to function as a leak prevention wall.

When the cover sheets 50 and 60 are separately attached as in the illustrated embodiment, there is an advantage that a degree of freedom in selecting a material is increased. However, there is a demerit that the number of materials and manufacturing processes is increased. For this reason, the folded part 20C obtained by folding back the outer body 20 on the inner surface of the diaper can be extended to the part overlapping the inner body 10 to form a part equivalent to the above-described cover sheets 50 and 60. Note that FIG. 3 illustrates an adhesive part 72 of the cover sheets 50 and 60 to the inner surface of the outer body 20.

(Dorsal Side Barrier)

On the inner surface of the underpants-type disposable diaper, a barrier sheet 71 is provided to extend from a position on the front side of the back end of the absorber 13 to the back side thereof and extend outward in the width direction from positions of the both side edges of the absorber 13 in the width direction WD. Though, as the barrier sheet 71, a dedicated sheet may be arranged, it is desirable to form the barrier sheet 71 by extending the cover sheet 60 to the crotch side as in the illustrated example. In the barrier sheet 71, a dimension of a part extending to the front side of the back end of the absorber 13 can be appropriately determined, and may be set to, for example, about 5 to 10% of a maximum length L of the product (about 40 to 80 mm in the case of an adult disposable diaper). A front end of the barrier sheet 71 can be located on the crotch side of the side seal portion 21.

As can be seen from the adhesive part 72 of the barrier sheet 71 (cover sheet 60) illustrated in FIG. 3, the barrier sheet 71 includes a free part 73 not bonded to a member on the back surface side and a fixed part 74 bonded to the member on the back surface side (the pressing sheet 20A and the folded part 20C in the illustrated example). The free part 73 is a part that is located at least in a middle of a part overlapping the absorber 13 in the width direction WD in the barrier sheet 71 and is continuous from a front edge to a middle in the front-back direction LD in the barrier sheet 71. In addition, the fixed part 74 surrounds a back side of the free part 73 and both sides of the free part 73 in the width direction WD, and width direction inner edges of parts located on both sides of the free part 73 in the width direction in the fixed part 74 are adjacent to width direction outer sides of the side edges of the inner body 10 and the side edges of the inner body 10. As illustrated in FIGS. 4 and 9, the barrier sheet 71 having the free part 73 and the fixed part 74 forms a pocket-shaped dorsal side barrier 70 having an inlet that opens on the crotch side. As illustrated in FIG. 13, in the fixed part 74, width direction inner edges of parts located on both sides of the free part 73 in the width direction WD are located on both sides in the width direction on the inner body 10 (located on the rising gather 90 in the illustrated example, and may be located on the top sheet 11 as long as the free part 73 is formed).

A dimension 73W of the free part 73 in the width direction WD may be substantially the same or narrower than a dimension 10W of the inner body 10 in the width direction WD. The dimension of the free part 73 in the width direction WD is equal to a width of an inlet of the dorsal side barrier 70, and thus a leakage prevention property becomes poor when the dimension is excessively narrow. Thus, the dimension is preferably 70 to 90% of the dimension 10W of the inner body 10 in the width direction WD.

A dimension 73L of the free part 73 in the front-back direction LD may be appropriately determined, and may be the same, longer than, or shorter than a dimension 70L of a region in which the barrier sheet 71 and the inner body 10 overlap in the front-back direction LD. When the dimension 73L of the free part 73 in the front-back direction LD is long, a pocket of the dorsal side barrier 70 becomes deep. However, when the dimension is excessively long, the barrier sheet 71 is likely to be irregularly deformed, and thus it is preferable that the part is located within a range of ±10 mm before and after a back edge of the absorber 13.

Characteristically, a torsion hardness (measurement method will be described later) of a predetermined part including the back end portion of the absorber 13 is set to 0.18 to 0.32 N·cm/cm, particularly preferably 0.22 to 0.28 N·cm/cm. When the torsion hardness of the predetermined part including the back end portion of the absorber 13 is within this range, as illustrated in FIG. 9, a part of the absorber 13 overlapping the free part 73 of the barrier sheet 71 gently bulges outward to circumscribe bulges of both gluteal regions, rippling deformation or bending deformation biting into an intergluteal cleft is less likely to occur, and contraction in the width direction WD becomes smaller. Further, the free part 73 of the barrier sheet 71 is raised on the opposite side from the bulge of the absorber 13 based on the strong absorber 13 that gently bulges outward to form the pocket-shaped dorsal side barrier 70 having the inlet that opens on the crotch side. Therefore, the inlet of the dorsal side barrier 70 is easily opened wider.

On the other hand, when the torsion hardness of the predetermined part including the back end portion of the absorber 13 is excessively weak, as illustrated in FIG. 14, a torsion force applied by movement of the legs and a contraction force in the width direction WD by the elastic member are applied to the part, so that rippling deformation or bending deformation biting into the intergluteal cleft occurs, and contraction in the width direction WD tends to increase. Further, in this case, the absorber 13 serving as a base of the barrier sheet 71 is less likely to bulge outward, and the width direction dimension of the free part 73 of the barrier sheet 71 becomes excessive, so that the free part 73 of the barrier sheet 71 becomes difficult to rise or is deformed in an irregular wavy pattern, and a situation in which the inlet or an inner space of the dorsal side barrier 70 becomes unnecessarily narrow is likely to occur.

As described above, when the part of the absorber 13 overlapping the free part 73 of the barrier sheet 71 easily contracts in the width direction WD, the situation in which the inlet or the inner space of the dorsal side barrier 70 becomes unnecessarily narrow is likely to occur. Therefore, it is preferable that the overlapping part between the free part 73 of the barrier sheet 71 and the absorber 13 does not have the stretchable region as in the outer body 20 of the illustrated example.

The absorber 13 is not limited by the material, etc. as long as the torsion hardness of the predetermined part including the back end portion is within the above-mentioned range. However, in the case of an aggregate of pulp fibers and super absorbent polymer particles, it is preferable that in the predetermined part including at least the back end portion, a total basis weight of the pulp fibers and the super absorbent polymer particles is 350 to 600 g/m², a weight ratio of the super absorbent polymer particles to the pulp fibers is 40 to 60%, and a thickness is 6 to 12 mm. In this way, by making the pulp basis weight sufficiently high and having a sufficient thickness, it is possible to obtain the absorber 13 having the above-mentioned torsion hardness.

As described above, in a case where the free part 73 of the barrier sheet 71 rises on the opposite side from the bulge of the absorber 13 based on the strong absorber 13 that gently bulges outward, even when the elastic member is not provided, the free part 73 of the barrier sheet 71 is slightly pushed toward the center side in the width direction WD, and thus naturally easily rises to the opposite side from the bulge of the absorber 13. Therefore, as in the example illustrated in FIGS. 4, 8 and 9, it is also preferable not to provide a stretchable part in the width direction WD contracted by the elastic member 75 in the free part 73 of the barrier sheet 71, thus simplifying the structure and thereby reducing the cost. Naturally, as illustrated in FIGS. 11 and 12, the elastic member 75 may be attached to the front end portion of the free part 73 of the barrier sheet 71 to raise the free part 73 by a contraction force of the elastic member 75.

In particular, in the case of not having the elastic member 75 for raising the free part 73 of the barrier sheet 71, when the barrier sheet 71 appears to merge into the surrounding member, for example, in a case where the free part 73 of the barrier sheet 71 is improperly bent, a user may not notice this fact during use, and there is concern that the leakage prevention effect may be insufficient. Therefore, as illustrated in FIGS. 1 and 3, it is also preferable to provide a mark 79 at the front end portion in the free part 73 of the barrier sheet 71 so that the presence of the barrier sheet 71 can be easily noticed. The mark 79 may be a straight line as in the illustrated example, or may be a pattern or any shape such as a mark or a character. The mark 79 may be provided by attaching a member to which the mark 79 is added or a member formed in the shape of the mark 79 to the free part 73. However, it is desirable to provide the mark 79 by directly printing the mark 79 on the free part 73.

In addition, in particular, in the case of not having the elastic member 75 for raising the free part 73 of the barrier sheet 71, there is concern that rising of the free part 73 of the barrier sheet 71 may be insufficient. In this case, as illustrated in FIGS. 1 and 9, it is preferable that the barrier sheet 71 is provided to pass over the rising gathers 90, and at least a part of the barrier sheet 71 is arranged to overlap the rising parts 94 of the rising gathers 90. In this way, the free part 73 of the barrier sheet 71 easily rises by the rising parts 94 of the rising gathers 90. In this case, a part of the barrier sheet 71 overlapping the rising gathers 90 may not be bonded to surfaces of the rising gathers 90 as illustrated in FIGS. 1 and 9 or may be bonded thereto as illustrated in FIG. 13. Naturally, as illustrated in FIG. 10, the free part 73 of the barrier sheet 71 may not be located at the rising parts 94 of the rising gathers 90 (the front end of the barrier sheet 71 is located at the fallen portions 93 of the rising gathers 90).

The material of the barrier sheet 71 is not particularly limited, and it is desirable to use the same material as that of the gather sheet 95. In particular, in the case of not having the elastic member for raising the free part 73 of the barrier sheet 71, when at least an outer surface of the barrier sheet 71 is a nonwoven fabric of fibers made of polyethylene resin, the barrier sheet 71 easily adheres to the skin, and rising of the free part 73 of the barrier sheet 71 is promoted, which is preferable. In addition, for the same reason, it is preferable that the barrier sheet 71 has high rigidity.

<Effect Confirmation Experiment>

Samples of the underpants-type disposable diaper illustrated in FIGS. 1 to 9, which were common except that the torsion hardness of the predetermined part including the back end portion of the absorber was different therebetween, were manufactured, and a state of the barrier sheet was observed with a dummy doll wearing each of the samples. The torsion hardness and the observation result of each sample are as follows.

(Sample 1)
Torsion hardness: 0.22 N·cm/cm
As in the example illustrated in FIG. 9, the free part of the barrier sheet rose to the opposite side from the bulge of the absorber, and the inlet of the dorsal side barrier reliably opened to the crotch side.

(Sample 2)
Torsion hardness: 0.28 N·cm/cm
As in the example illustrated in FIG. 9, the free part of the barrier sheet rose to the opposite side from the bulge of the absorber, and the inlet of the dorsal side barrier reliably opened to the crotch side.

(Sample 3)
Torsion hardness: 0.15 N·cm/cm
As in the example illustrated in FIG. 14, contraction of the absorber in the width direction became large, and the absorber serving as the base of the barrier sheet was less likely to bulge outward. As a result, the inlet of the dorsal side barrier collapsed and became narrow.

(Sample 4)
Torsion hardness: 0.35 N·cm/cm
The absorber was not deformed as in the example illustrated in FIG. 14. However, the absorber hardly gently bulged outward, and the inlet of the dorsal side barrier was narrower than that of Samples 1 and 2.

<Description of Terms Used Herein>

In a case where the following terms are used in the specification, those have the following meanings unless otherwise specified in the specification.

"Front-back direction" means a direction (vertical direction) indicated by the reference character LD in the figure, "width direction" means a direction (right-left direction) indicated by WD in the figure, and the front-back direction and the width direction are orthogonal to each other.

"Spread state" means a flatly spread state without contraction or slack.

"Stretch rate" means the value when the natural length is taken as 100%. For example, a stretch rate of 200% is synonymous with a stretch magnification of 2 times.

"Basis weight" is measured as follows. After the sample or test piece is preliminary dried, it is allowed to stand in a test room or apparatus under normal conditions (the test location is at a temperature: 23±1° C., relative humidity: 50±2%) until the constant mass. The preliminary drying is to make the sample or test piece be constant mass in an environment of a temperature of 100° C. Note that the fibers of an official moisture regain of 0.0% do not need preliminary drying. From a test piece having a constant weight, a sample having a size of 100 mm×100 mm is cut out using a template for sampling (100 mm×100 mm) per square meter. The sample is weighed and the weight is multiplied by 100 into the weight per square meter. The resulting value is defined as the basis weight.

"Torsion hardness" means a value measured by the following test. In order to apply as little force as possible to the absorber, a part having a front-back direction dimension 60 mm×a width direction dimension 140 mm is cut out to include the back end of the absorber, and the whole is wrapped with a single layer of crepe paper (basis weight 15 g/m$^2$) to manufacture a specimen. Using a torsion tester (KES-YN-1-B, manufactured by KATO TECH CO., LTD.), both end portions of the specimen in the width direction are pinched with a chuck having a chuck distance of 110 mm, and a maximum load (torsion hardness) when twisted by 70 degrees around a longitudinal center axis is measured. Conditions of the tester are SENS (recording sensitivity): 10, torsion angle: 7, CONTROL: 7, speed: 12 cm/s. Note that the test is performed on five specimens, and an average value is used as a measured value of the torsion hardness.

"Thickness" of the absorber is measured using a thickness measuring instrument of OZAKI MFG. CO., LTD. (PEACOCK, digital type, model FFD-7 (measurement range 0 to 20 mm)) by making the sample and the thickness measuring instrument horizontal.

"Thickness" other than the above thickness is automatically measured using an automatic thickness measuring instrument (KES-G5 Handy Compression Measurement Program) under the conditions of load: 0.098 N/cm² and pressurized area: 2 cm².

"Water absorption capacity" is measured according to JIS K7223-1996 "Testing method for water absorption capacity of super absorbent polymers".

"Water absorption rate" is the "time that elapses before the end point" measured in accordance with JIS K7224-1996 "Testing method for water absorption rate of super absorbent polymers" has been carried out using 2 g of superabsorbent polymer and 50 g of physiological saline solution.

When environmental conditions in tests and measurements are not described, the tests and measurements shall be carried out in a test room or apparatus under normal conditions (the test location is at a temperature: 23±1° C., relative humidity: 50±2%).

The dimension of each part means the dimension in the spread state, not the natural length state, unless otherwise specified.

INDUSTRIAL APPLICABILITY

The invention can be used for the underpants-type disposable diaper as in the above example.

REFERENCE SIGNS LIST

10 INNER BODY
11 TOP SHEET
12 LIQUID IMPERVIOUS SHEET
13 ABSORBER
14 WRAPPING SHEET
20 OUTER BODY
20C FOLDED PART
21 SIDE SEAL PORTION
24 WAIST PORTION ELASTIC MEMBER
25 LOWER WAIST PORTION ELASTIC MEMBER
26, 27 CURVED ELASTIC MEMBER
26 DORSAL SIDE CURVED ELASTIC MEMBER
27 VENTRAL SIDE CURVED ELASTIC MEMBER
29 AROUND-LEG LINE
90 RISING GATHER
91 GATHER FIXED PORTION
92 MAIN UNIT PART
93 FALLEN PORTION
94 RISING PART
95 GATHER SHEET
96 GATHER ELASTIC MEMBER
F FRONT BODY
B BACK BODY
LD FRONT-BACK DIRECTION
WD WIDTH DIRECTION
70 DORSAL SIDE BARRIER
71 BARRIER SHEET
73 FREE PART
74 FIXED PART
75 ELASTIC MEMBER
79 MARK

The invention claimed is:

1. An underpants-type disposable diaper comprising:
an integral outer body extending over a front body and a back body or an outer body separately provided to the front body and the back body;
side seal portions obtained by bonding both side portions of the outer body in the front body and both side portions of the outer body in the back body, respectively;
a waist opening and a pair of right and left leg openings;
a front lower torso region of the outer body in the front body, determined as a front-back direction region having the side seal portions;
a back lower torso region of the outer body in the back body, determined as a front-back direction region having the side seal portions;
an inner body attached to an intermediate portion in a width direction of the outer body, the inner body extending from the front lower torso region to the back lower torso region;
an absorber contained in the inner body, the absorber extending from the front lower torso region to the back lower torso region;
a stretchable region contracted in the width direction on a waist side of a back end portion of the absorber in the back lower torso region, the stretchable region extending forward up to a position to overlap the inner body; and
a barrier sheet that extends from forward of to backward of a back end of the absorber and extends from both side edges in the width direction of the absorber outward in the width direction,
wherein the barrier sheet has a free part not bonded to a member on a back surface side and a fixed part bonded to the member on the back surface side,
the free part is located at least in a middle in the width direction of a part of the barrier sheet that overlaps the absorber and is continuous from a front edge to a middle in a front-back direction of the barrier sheet,
a back end of the inner body is positioned backward of the back end of the absorber, and a back end of the free part is positioned between the back end of the inner body and the back end of the absorber,
the fixed part extends backward from the back end of the free part,
the fixed part further surrounds both sides in the width direction of the free part, and a width direction inner edge of a part of the fixed part that is located on both sides in the width direction of the free part is on an outer side of a side edge of the inner body in the width direction and adjacent to the side edge of the inner body or is located on the inner body,
a pocket-shaped dorsal side barrier having an inlet opening on a crotch side is formed with the free part of the barrier sheet being raised while a part of the absorber that overlaps the free part of the barrier sheet being curved to bulge outward to prevent back leakage from the underpants-type disposable diaper,
a torsion hardness of a predetermined part including the back end portion of the absorber is 0.18 to 0.32 N·cm/cm, and
the outer body does not have the stretchable region in its part where the free part of the barrier sheet and the absorber overlap the outer body.

2. The underpants-type disposable diaper according to claim 1, wherein in the predetermined part including the back end portion of the absorber, a total basis weight of pulp fibers and super absorbent polymer particles is 350 to 600 g/m², a weight ratio of the super absorbent polymer particles to the pulp fibers is 40 to 60%, and a thickness is 6 to 12 mm.

3. The underpants-type disposable diaper according to claim 2, wherein the free part of the barrier sheet does not have a stretchable part in the width direction contracted by an elastic member.

4. The underpants-type disposable diaper according to claim 1, wherein the free part of the barrier sheet is free of a stretchable part in the width direction contracted by an elastic member.

5. The underpants-type disposable diaper according to claim 4, wherein a mark is provided to a front end portion in the free part of the barrier sheet.

6. The underpants-type disposable diaper according to claim 5,
wherein the inner body has rising gathers that rise from both sides in the width direction,
each of the rising gathers has a main unit part extending from both side portions of a surface of the inner body to a center side in the width direction, a fallen portion which is a part fixed to the surface of the inner body in a fallen state of both end portions of the main unit part in the front-back direction, a non-fixed rising part located between front and back fallen portions, and a gather elastic member provided along the front-back direction at least at a tip portion of the rising part,
the barrier sheet is provided to pass over the rising gathers, and
at least a part of the barrier sheet overlaps the rising parts of the rising gathers.

7. The underpants-type disposable diaper according to claim 5, wherein at least an outer surface of the barrier sheet is a nonwoven fabric of fibers which is made of polyethylene resin.

8. The underpants-type disposable diaper according to claim 4,
wherein the inner body has rising gathers that rise from both sides in the width direction,
each of the rising gathers has a main unit part extending from both side portions of a surface of the inner body to a center side in the width direction, a fallen portion which is a part fixed to the surface of the inner body in a fallen state of both end portions of the main unit part in the front-back direction, a non-fixed rising part located between front and back fallen portions, and a gather elastic member provided along the front-back direction at least at a tip portion of the rising part,
the barrier sheet is provided to pass over the rising gathers, and
at least a part of the barrier sheet overlaps the rising parts of the rising gathers.

9. The underpants-type disposable diaper according to claim 8, wherein at least an outer surface of the barrier sheet is a nonwoven fabric of fibers which is made of polyethylene resin.

10. The underpants-type disposable diaper according to claim 4, wherein at least an outer surface of the barrier sheet is a nonwoven fabric of fibers which is made of polyethylene resin.

* * * * *